United States Patent
Zhang et al.

(10) Patent No.: US 11,957,913 B2
(45) Date of Patent: Apr. 16, 2024

(54) SYSTEMS AND METHODS FOR BURST WAVEFORMS WITH ANODIC-LEADING PULSES

(71) Applicant: Advanced Neuromodulation Systems, Inc., Plano, TX (US)

(72) Inventors: Simeng Zhang, Frisco, TX (US); Hyun-Joo Park, Frisco, TX (US); Filippo Agnesi, Plano, TX (US); Yagna Pathak, Skokie, IL (US); Erika Ross, Dallas, TX (US)

(73) Assignee: Advanced Neuromodulation Systems, Inc., Plano, TX (US)

( * ) Notice: Subject to any disclaimer, the term of this patent is extended or adjusted under 35 U.S.C. 154(b) by 0 days.

(21) Appl. No.: 18/143,206

(22) Filed: May 4, 2023

(65) Prior Publication Data

US 2023/0271014 A1    Aug. 31, 2023

Related U.S. Application Data

(63) Continuation of application No. 17/082,299, filed on Oct. 28, 2020, now Pat. No. 11,679,264.

(60) Provisional application No. 63/075,906, filed on Sep. 9, 2020.

(51) Int. Cl.
*A61N 1/36* (2006.01)
*A61N 1/05* (2006.01)

(52) U.S. Cl.
CPC ....... *A61N 1/36178* (2013.01); *A61N 1/0551* (2013.01); *A61N 1/36175* (2013.01); *A61N 1/36071* (2013.01)

(58) Field of Classification Search
CPC .............. A61N 1/36178; A61N 1/0551; A61N 1/36175; A61N 1/36071; A61N 1/36157
See application file for complete search history.

(56) References Cited

U.S. PATENT DOCUMENTS

| | | |
|---|---|---|
| 7,212,110 B1 | 5/2007 | Martin et al. |
| 7,228,179 B2 | 6/2007 | Campen et al. |
| 7,571,007 B2 | 8/2009 | Erickson et al. |
| 7,734,340 B2 | 6/2010 | De Ridder |
| 8,224,453 B2 | 7/2012 | De Ridder |
| 8,364,273 B2 | 1/2013 | De Ridder |
| 2006/0170486 A1 | 8/2006 | Tranchina et al. |

(Continued)

FOREIGN PATENT DOCUMENTS

WO    2001093953 A1    12/2001

OTHER PUBLICATIONS

Kevin C. Stieger et al., "In vivo microstimulation with cathodic and anodic asymmetric waveforms modulates spatiotemporal calcium dynamics in cortical neuropil and pyramidal neurons of male mice", J Neurosci Res. 2020; 98:2072-2095 (2020).

(Continued)

*Primary Examiner* — Paula J Stice
(74) *Attorney, Agent, or Firm* — Armstrong Teasdale LLP

(57) ABSTRACT

The present disclosure provides systems and methods for generating burst waveforms. An implantable neurostimulation system includes an implantable stimulation lead including a plurality of contacts, and an implantable pulse generator communicatively coupled to the stimulation lead. The pulse generator is configured to generate a waveform including a burst that includes a leading anodic pulse followed by alternating cathodic pulses and anodic pulses, each cathodic pulse in the burst having a greater amplitude than the previous cathodic pulse.

20 Claims, 5 Drawing Sheets

(56) References Cited

U.S. PATENT DOCUMENTS

| | | |
|---|---|---|
| 2008/0294211 A1 | 11/2008 | Moffitt |
| 2009/0326608 A1 | 12/2009 | Huynh et al. |
| 2015/0335898 A1 | 11/2015 | Carlson et al. |
| 2017/0173335 A1 | 6/2017 | Min et al. |
| 2018/0289965 A1 | 10/2018 | Nelson et al. |
| 2020/0147390 A1 | 5/2020 | Zhang et al. |

OTHER PUBLICATIONS

International Search Report and Written Opinion, PCT/US2021/049335, dated Dec. 20, 2021, 28 pages.

SYSTEMS AND METHODS FOR BURST WAVEFORMS WITH ANODIC-LEADING PULSES

CROSS REFERENCE TO RELATED APPLICATIONS

This application is a continuation of U.S. patent application Ser. No. 17/082,299, now U.S. Pat. No. 11,679,246, filed Oct. 28, 2020, which claims priority to provisional application Ser. No. 63/075,906, filed Sep. 9, 2020, both of which are incorporated herein by reference in their entirety.

A. FIELD OF THE DISCLOSURE

The present disclosure relates generally to neurostimulation systems, and more particularly to burst waveforms for neurostimulation systems.

B. BACKGROUND ART

Neurostimulation is an established neuromodulation therapy for the treatment of chronic pain and movement disorders. For example, neurostimulation has been shown to improve cardinal motor symptoms of Parkinson's Disease (PD), such as bradykinesia, rigidity, and tremors. Types of neurostimulation include deep brain stimulation (DBS), spinal cord stimulation (SCS), peripheral nerve stimulation, and Dorsal Root Ganglion (DRG) stimulation.

Burst waveforms have demonstrated success in SCS, and are actively being investigated in DRG stimulation and DBS therapies. A burst waveform typically includes a "burst" including a plurality of pulses each having an associated pulse width, with an intra-burst frequency defining the timing between the plurality of pulses within the burst. The burst repeats at an inter-burst frequency.

At least some known burst waveforms include cathodic-leading pulses, because cathodic-leading pulses may be more likely to activate axons near the electrode applying the simulation. However, it may be possible to achieve equal or improved success using anodic-leading pulses.

BRIEF SUMMARY OF THE DISCLOSURE

In one embodiment, the present disclosure is directed to an implantable neurostimulation system for generating burst waveforms. The neurostimulation system includes an implantable stimulation lead including a plurality of contacts, and an implantable pulse generator communicatively coupled to the stimulation lead and configured to generate a waveform including a burst that includes a leading anodic pulse followed by alternating cathodic pulses and anodic pulses, each cathodic pulse in the burst having a greater amplitude than the previous cathodic pulse.

In another embodiment, the present disclosure is directed to an implantable pulse generator for generating burst waveforms. The pulse generator includes a memory device, and a processor coupled to the memory device, the processor configured to generate a waveform including a burst that includes a leading anodic pulse followed by alternating cathodic pulses and anodic pulses, each cathodic pulse in the burst having a greater amplitude than the previous cathodic pulse.

In another embodiment, the present disclosure is directed to a method of applying neurostimulation. The method includes generating, using an implantable pulse generator, a waveform including a burst that includes a leading anodic pulse followed by alternating cathodic pulses and anodic pulses, each cathodic pulse in the burst having a greater amplitude than the previous cathodic pulse, and applying the waveform to a patient using an implantable stimulation lead coupled to the implantable pulse generator.

The foregoing and other aspects, features, details, utilities and advantages of the present disclosure will be apparent from reading the following description and claims, and from reviewing the accompanying drawings.

BRIEF DESCRIPTION OF THE DRAWINGS

Corresponding reference characters indicate corresponding parts throughout the several views of the drawings.

DETAILED DESCRIPTION OF THE DISCLOSURE

The present disclosure provides systems and methods for generating burst waveforms. An implantable neurostimulation system includes an implantable stimulation lead including a plurality of contacts, and an implantable pulse generator communicatively coupled to the stimulation lead. The pulse generator is configured to generate a waveform including a burst that includes a leading anodic pulse followed by alternating cathodic pulses and anodic pulses, each cathodic pulse in the burst having a greater amplitude than the previous cathodic pulse.

Neurostimulation systems are devices that generate electrical pulses and deliver the pulses to nervous tissue of a patient to treat a variety of disorders. One category of neurostimulation systems is deep brain stimulation (DBS). In DBS, pulses of electrical current are delivered to target regions of a subject's brain, for example, for the treatment of movement and effective disorders such as PD and essential tremor. Another category of neurostimulation systems is spinal cord stimulation (SCS) which is often used to treat chronic pain such as Failed Back Surgery Syndrome (FBSS) and Complex Regional Pain Syndrome (CRPS).

Neurostimulation systems generally include a pulse generator and one or more leads. A stimulation lead includes a lead body of insulative material that encloses wire conductors. The distal end of the stimulation lead includes multiple electrodes, or contacts, that intimately impinge upon patient tissue and are electrically coupled to the wire conductors. The proximal end of the lead body includes multiple terminals (also electrically coupled to the wire conductors) that are adapted to receive electrical pulses. In DBS systems, the distal end of the stimulation lead is implanted within the brain tissue to deliver the electrical pulses. The stimulation leads are then tunneled to another location within the patient's body to be electrically connected with a pulse generator or, alternatively, to an "extension." The pulse generator is typically implanted in the patient within a subcutaneous pocket created during the implantation procedure.

The pulse generator is typically implemented using a metallic housing (or can) that encloses circuitry for generating the electrical stimulation pulses, control circuitry, communication circuitry, a rechargeable or primary cell battery, etc. The pulse generating circuitry is coupled to one or more stimulation leads through electrical connections provided in a "header" of the pulse generator. Specifically, feedthrough wires typically exit the metallic housing and enter into a header structure of a moldable material. Within the header structure, the feedthrough wires are electrically coupled to annular electrical connectors. The header structure holds the annular connectors in a fixed arrangement that corresponds to the arrangement of terminals on the proximal end of a stimulation lead.

Figure 1:
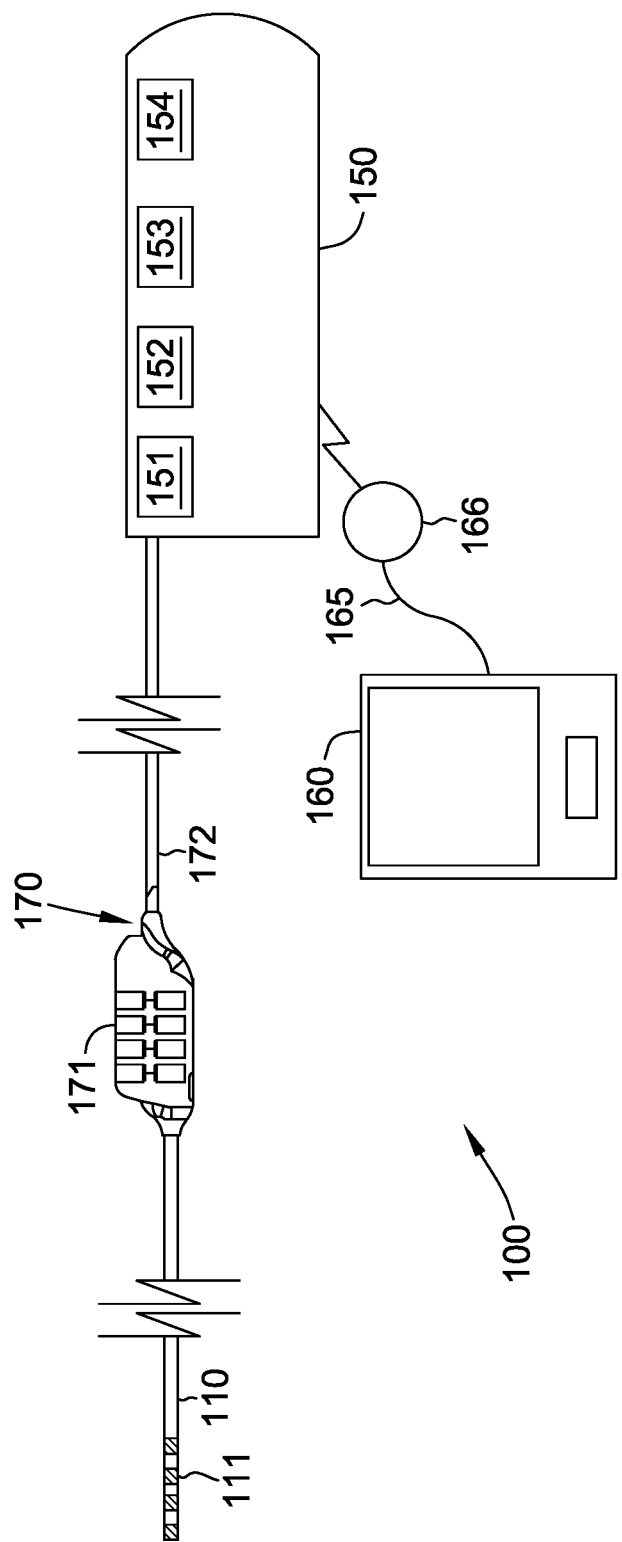
FIG. 1 is a schematic view of one embodiment of a stimulation system.

Referring now to the drawings, and in particular to FIG. 1, a stimulation system is indicated generally at 100. Stimulation system 100 generates electrical pulses for application to tissue of a patient, or subject, according to one embodiment. System 100 includes an implantable pulse generator (IPG) 150 that is adapted to generate electrical pulses for application to tissue of a patient. Alternatively, system 100 may include an external pulse generator (EPG) positioned outside the patient's body. IPG 150 typically includes a metallic housing (or can) that encloses a controller 151, pulse generating circuitry 152, a battery 153, far-field and/or near field communication circuitry 154, and other appropriate circuitry and components of the device. Controller 151 typically includes a microcontroller or other suitable processor for controlling the various other components of the device. Software code is typically stored in memory of IPG 150 for execution by the microcontroller or processor to control the various components of the device.

IPG 150 may comprise one or more attached extension components 170 or be connected to one or more separate extension components 170. Alternatively, one or more stimulation leads 110 may be connected directly to IPG 150. Within IPG 150, electrical pulses are generated by pulse generating circuitry 152 and are provided to switching circuitry. The switching circuit connects to output wires, traces, lines, or the like (not shown) which are, in turn, electrically coupled to internal conductive wires (not shown) of a lead body 172 of extension component 170. The conductive wires, in turn, are electrically coupled to electrical connectors (e.g., "Bal-Seal" connectors) within connector portion 171 of extension component 170. The terminals of one or more stimulation leads 110 are inserted within connector portion 171 for electrical connection with respective connectors. Thereby, the pulses originating from IPG 150 and conducted through the conductors of lead body 172 are provided to stimulation lead 110. The pulses are then conducted through the conductors of lead 110 and applied to tissue of a patient via electrodes 111. Any suitable known or later developed design may be employed for connector portion 171.

For implementation of the components within IPG 150, a processor and associated charge control circuitry for an implantable pulse generator is described in U.S. Pat. No. 7,571,007, entitled "SYSTEMS AND METHODS FOR USE IN PULSE GENERATION," which is incorporated herein by reference. Circuitry for recharging a rechargeable battery of an implantable pulse generator using inductive coupling and external charging circuits are described in U.S. Pat. No. 7,212,110, entitled "IMPLANTABLE DEVICE AND SYSTEM FOR WIRELESS COMMUNICATION," which is incorporated herein by reference.

An example and discussion of "constant current" pulse generating circuitry is provided in U.S. Patent Publication No. 2006/0170486 entitled "PULSE GENERATOR HAVING AN EFFICIENT FRACTIONAL VOLTAGE CONVERTER AND METHOD OF USE," which is incorporated herein by reference. One or multiple sets of such circuitry may be provided within IPG 150. Different pulses on different electrodes may be generated using a single set of pulse generating circuitry using consecutively generated pulses according to a "multi-stimset program" as is known in the art. Alternatively, multiple sets of such circuitry may be employed to provide pulse patterns that include simultaneously generated and delivered stimulation pulses through various electrodes of one or more stimulation leads as is also known in the art. Various sets of parameters may define the pulse characteristics and pulse timing for the pulses applied to various electrodes as is known in the art. Although constant current pulse generating circuitry is contemplated for some embodiments, any other suitable type of pulse generating circuitry may be employed such as constant voltage pulse generating circuitry.

Stimulation lead(s) 110 may include a lead body of insulative material about a plurality of conductors within the material that extend from a proximal end of lead 110 to its distal end. The conductors electrically couple a plurality of electrodes 111 to a plurality of terminals (not shown) of lead 110. The terminals are adapted to receive electrical pulses and the electrodes 111 are adapted to apply stimulation pulses to tissue of the patient. Also, sensing of physiological signals may occur through electrodes 111, the conductors, and the terminals. Additionally or alternatively, various sensors (not shown) may be located near the distal end of stimulation lead 110 and electrically coupled to terminals through conductors within the lead body 172. Stimulation lead 110 may include any suitable number and type of electrodes 111, terminals, and internal conductors.

Controller device 160 may be implemented to recharge battery 153 of IPG 150 (although a separate recharging device could alternatively be employed). A "wand" 165 may be electrically connected to controller device through suitable electrical connectors (not shown). The electrical connectors are electrically connected to coil 166 (the "primary" coil) at the distal end of wand 165 through respective wires (not shown). Typically, coil 166 is connected to the wires through capacitors (not shown). Also, in some embodiments, wand 165 may comprise one or more temperature sensors for use during charging operations.

The patient then places the primary coil 166 against the patient's body immediately above the secondary coil (not shown), i.e., the coil of the implantable medical device. Preferably, the primary coil 166 and the secondary coil are aligned in a coaxial manner by the patient for efficiency of the coupling between the primary and secondary coils. Controller device 160 generates an AC-signal to drive current through coil 166 of wand 165. Assuming that primary coil 166 and secondary coil are suitably positioned relative to each other, the secondary coil is disposed within the magnetic field generated by the current driven through primary coil 166. Current is then induced by a magnetic field in the secondary coil. The current induced in the coil of the implantable pulse generator is rectified and regulated to recharge the battery of IPG 150. The charging circuitry may also communicate status messages to controller device 160 during charging operations using pulse-loading or any other suitable technique. For example, controller device 160 may communicate the coupling status, charging status, charge completion status, etc.

External controller device 160 is also a device that permits the operations of IPG 150 to be controlled by a user after IPG 150 is implanted within a patient, although in alternative embodiments separate devices are employed for charging and programming. Also, multiple controller devices may be provided for different types of users (e.g., the patient or a clinician). Controller device 160 can be implemented by utilizing a suitable handheld processor-based system that possesses wireless communication capabilities. Software is typically stored in memory of controller device 160 to control the various operations of controller device 160. Also, the wireless communication functionality of controller device 160 can be integrated within the handheld device package or provided as a separate attachable device. The interface functionality of controller device 160 is implemented using suitable software code for interacting with the user and using the wireless communication capabilities to conduct communications with IPG 150.

Controller device 160 preferably provides one or more user interfaces to allow the user to operate IPG 150 according to one or more stimulation programs to treat the patient's disorder(s). Each stimulation program may include one or more sets of stimulation parameters including pulse amplitude, pulse width, pulse frequency or inter-pulse period, pulse repetition parameter (e.g., number of times for a given pulse to be repeated for respective stimset during execution of program), etc. In the methods and systems described herein, stimulation parameters may include, for example, a number of pulses in a burst (e.g., 3, 4, or 5 pulses per burst), an intra-burst frequency (e.g., 500 Hz), an inter-burst frequency (e.g., 40 Hz), and a delay between the pulses in a burst (e.g., less than 1 millisecond (ms)).

IPG 150 modifies its internal parameters in response to the control signals from controller device 160 to vary the stimulation characteristics of stimulation pulses transmitted through stimulation lead 110 to the tissue of the patient. Neurostimulation systems, stimsets, and multi-stimset programs are discussed in PCT Publication No. WO 2001/093953, entitled "NEUROMODULATION THERAPY SYSTEM," and U.S. Pat. No. 7,228,179, entitled "METHOD AND APPARATUS FOR PROVIDING COMPLEX TISSUE STIMULATION PATTERNS," which are incorporated herein by reference. Example commercially available neurostimulation systems include the EON MINI™ pulse generator and RAPID PROGRAMMER™ device from Abbott Laboratories.

The systems and methods described herein facilitate generating and delivering burst stimulation waveforms with anodic-leading pulses. These stimuli may be stored in a generator (e.g., IPG 150 or an external pulse generator), such that the generator ensures that each pulse is delivered in a specific order, after a specific interval following a previous pulse, with each pulse having a specific amplitude and duration. The waveforms described herein may provide improved stimulation in DBS, SCS, peripheral nerve stimulation, and DRG stimulation systems.

Figure 2:
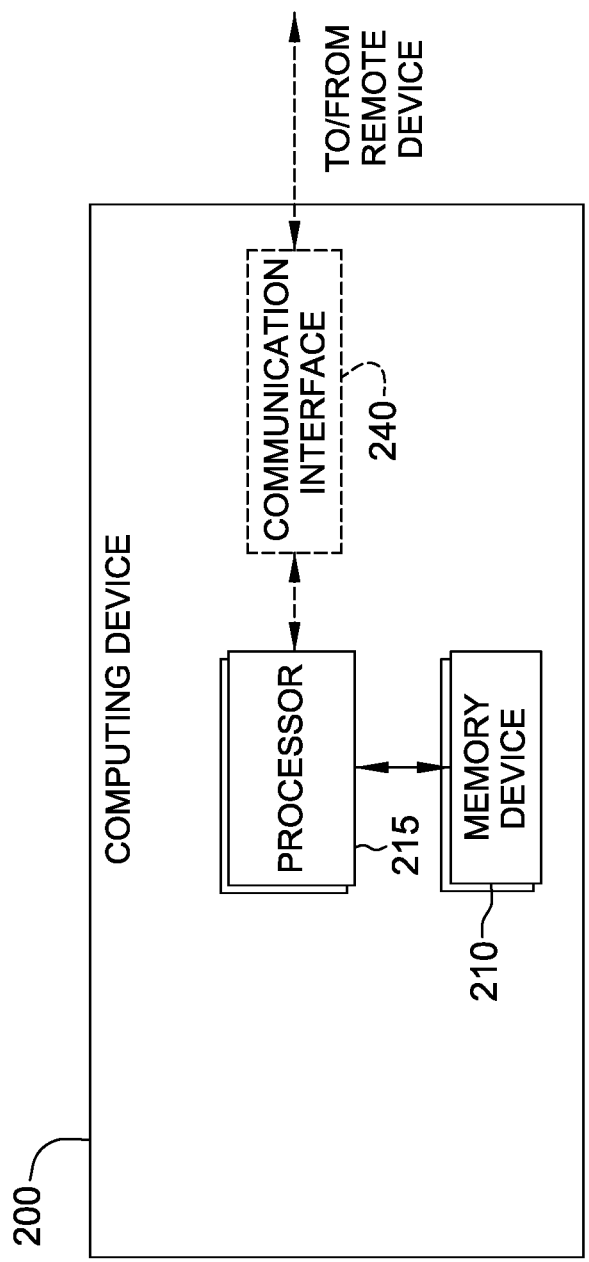
FIG. 2 is a block diagram of one embodiment of a computing device that may be used with the stimulation system shown in FIG. 1.

FIG. 2 is a block diagram of one embodiment of a computing device 200 that may be used to generate burst stimulation waveforms as described herein. Computing device 200 may be included, for example, within an IPG (e.g., IPG 150) or an external pulse generator.

In this embodiment, computing device 200 includes at least one memory device 210 and a processor 215 that is coupled to memory device 210 for executing instructions. In some embodiments, executable instructions are stored in memory device 210. In the illustrated embodiment, computing device 200 performs one or more operations described herein by programming processor 215. For example, processor 215 may be programmed by encoding an operation as one or more executable instructions and by providing the executable instructions in memory device 210.

Processor 215 may include one or more processing units (e.g., in a multi-core configuration). Further, processor 215 may be implemented using one or more heterogeneous processor systems in which a main processor is present with secondary processors on a single chip. In another illustrative example, processor 215 may be a symmetric multi-processor system containing multiple processors of the same type. Further, processor 215 may be implemented using any suitable programmable circuit including one or more systems and microcontrollers, microprocessors, reduced instruction set circuits (RISC), application specific integrated circuits (ASIC), programmable logic circuits, field programmable gate arrays (FPGA), and any other circuit capable of executing the functions described herein.

In the illustrated embodiment, memory device 210 is one or more devices that enable information such as executable instructions and/or other data to be stored and retrieved. Memory device 210 may include one or more computer readable media, such as, without limitation, dynamic random access memory (DRAM), read-only memory (ROM), electrically erasable programmable read-only memory (EEPROM), static random access memory (SRAM), a solid state disk, and/or a hard disk. Memory device 210 may be configured to store, without limitation, application source code, application object code, source code portions of interest, object code portions of interest, configuration data, execution events and/or any other type of data.

Computing device 200, in the illustrated embodiment, includes a communication interface 240 coupled to processor 215. Communication interface 240 communicates with one or more remote devices, such as a clinician or patient programmer. To communicate with remote devices, communication interface 240 may include, for example, a wired network adapter, a wireless network adapter, a radio-frequency (RF) adapter, and/or a mobile telecommunications adapter.

As noted above, burst waveforms have demonstrated success in SCS, and are actively being investigated in DRG stimulation and DBS therapies.

Figure 3:
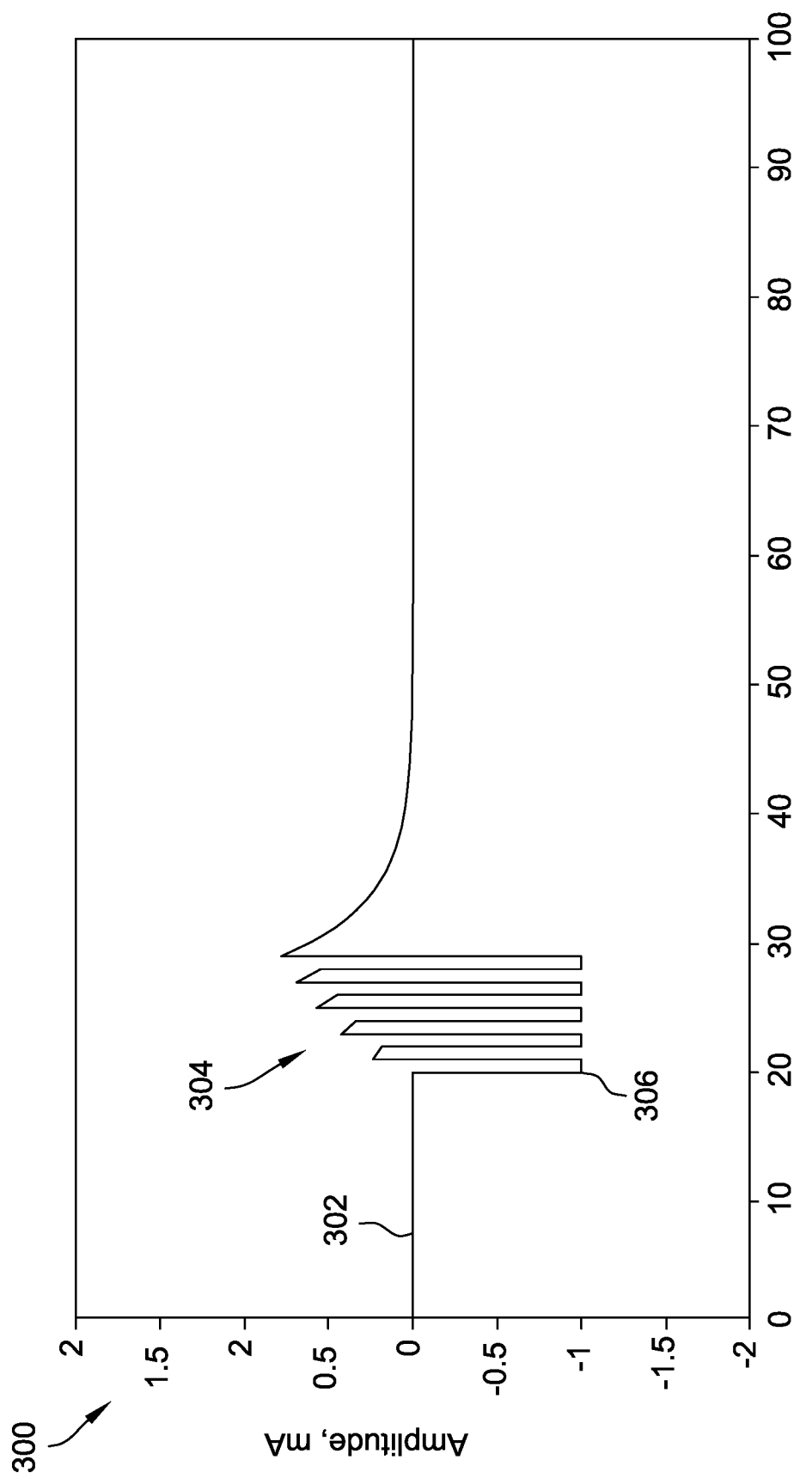
FIG. 3 is a graph illustrating an example of a first known burst waveform.

FIG. 3 is a graph 300 illustrating an example of a first known burst waveform 302. In this example, waveform 302 includes a burst 304 of five pulses 306 that are passively charged cathodic pulses, with each pulse having a width of 1000 microseconds (μs). Cathodic pulses are generated by active circuitry of the implantable pulse generator as opposed to mere passive discharge of built-up charge as observed in some known spinal cord stimulation systems. An intra-burst frequency between pulses 306 in burst 304 is set to 500 Hz for SCS, and may be adjusted for DRG stimulation, peripheral nerve stimulation, and DBS applications. Further, in this example, burst 304 repeats at an inter-burst frequency of 40 Hz for SCS applications, which may be adjusted based on user preferences or for other applications.

Figure 4:
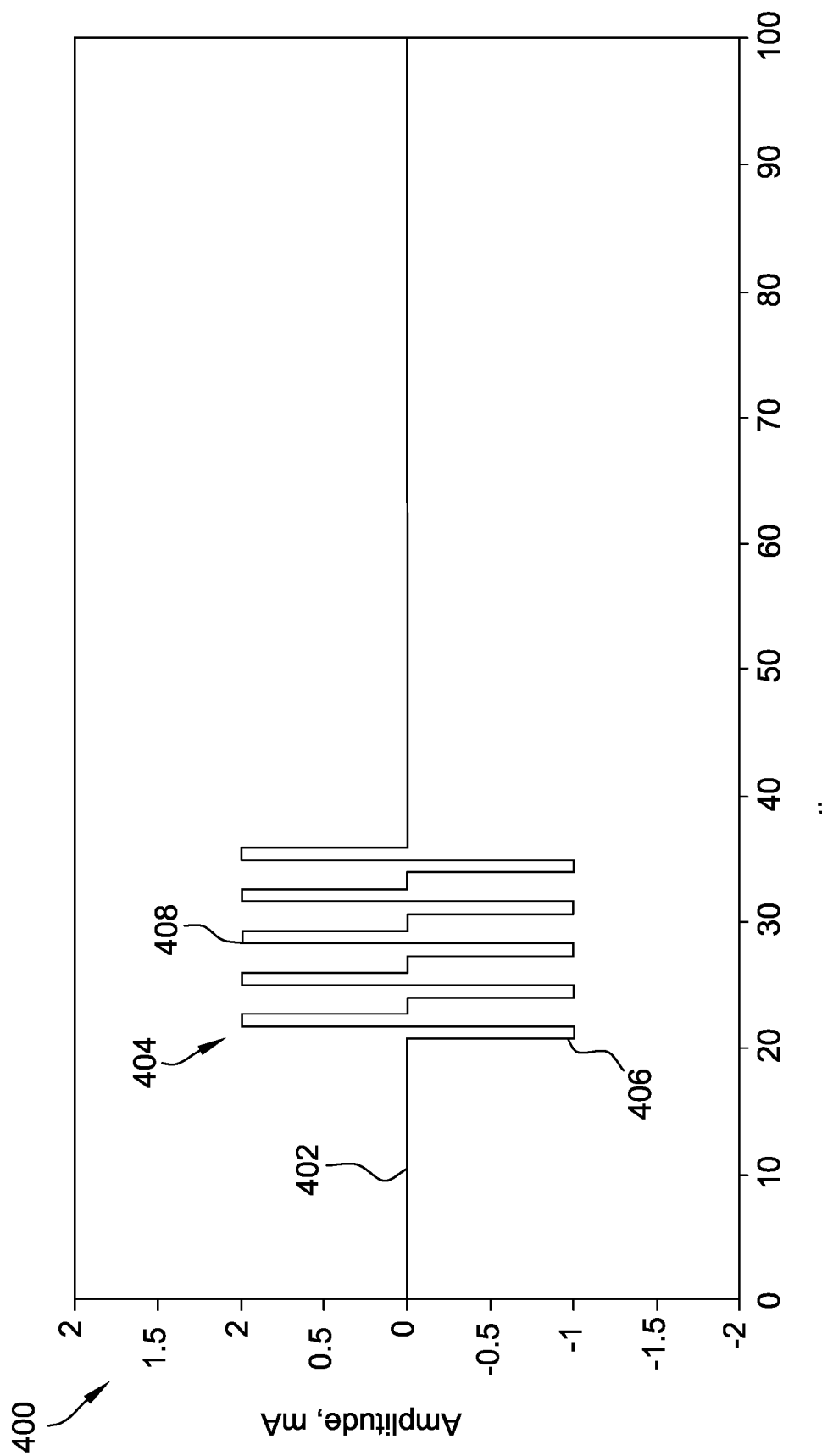
FIG. 4 is a graph illustrating an example of a second known burst waveform.

FIG. 4 is a graph 400 illustrating an example of a second known burst waveform 402. Waveform 402 includes a burst 404 of five pulses 406 that are cathodic pulses, with each pulse having a width of 1000 μs. Waveform 402 includes an intra-burst frequency of 300 Hz.

Waveform 402 differs from waveform 302 in multiple ways. For example, waveform 302 uses a relatively long pulse width combined with a relatively high intra-burst frequency to assure progressive charge accumulation within bursts 304. Further, waveform 302 employs passive discharge, which also ensures charge accumulation within bursts 304. In contrast, in waveform 402, each pulse 406 is completely discharged with active symmetric anodic square pulses 408. Overall, the charge accumulation within bursts 304 of waveform 302 guarantees a non-linear charge buildup, which may be advantageous over waveform 402.

At least some known stimulation schemes (such as waveform 302 and waveform 402) use cathodic-leading pulses because they are more likely than anodic-leading pulses to activate axons nearby the stimulation electrode. This may suggest that anodic-leading pulses are less effective, or require higher current amplitude to function properly. However, not all anodic-leading pulses are equivalent.

For example, if an anodic-leading pulse has a relatively small amplitude and a relatively long pulse width, the pulse will not activate any axons (instead, it will hyperpolarize some axons), such that a second, subsequent cathodic pulse activates axons. This may be referred to as "anodic break stimulation". That is, the leading anodic pulse acts as a pre-conditioning pulse for the subsequent cathodic pulse. This stimulation scheme has been demonstrated to effectively activate neuronal elements near the electrode, comparable to results observed when using cathodic-leading pulses. For example, various waveforms and their effects on neuronal activation near the stimulation electrode are shown and described in "In vivo microstimulation with cathodic and anodic asymmetric waveforms modulates spatiotemporal calcium dynamics in cortical neuropil and pyramidal neurons of male mice" by Kevin C. Stieger et al. in *J Neurosci Res.* 2020; 98:2072-2095 (2020).

One advantage of using an anodic break stimulation scheme is that the scheme can activate both neurons near the electrode and distal neurons whose fibers of passage pass by the electrode. This may be particularly desirable for many neuromodulation applications. For example, in DBS for the subthalamic nucleus (STN), both the STN cells and fibers that pass by the STN can provide therapy for alleviating Parkinsonian symptoms. Therefore, if a stimulation scheme can activate both the neurons nearby and the passing fibers, it may be a desirable stimulation scheme.

As described in detail below, the systems and methods described herein provide a waveform with an anodic-leading pulse and progressively growing cathodic pulses. This waveform may be referred to as an "anodic-leading progressive burst". The waveform mimics the bursting and charge buildup of waveform 302, but also takes advantage of the anodic break stimulation scheme. This has the potential to activate more neuronal elements near the site of stimulation, while also providing the advantageous non-linear charge buildup of waveform 302.

Figure 5:
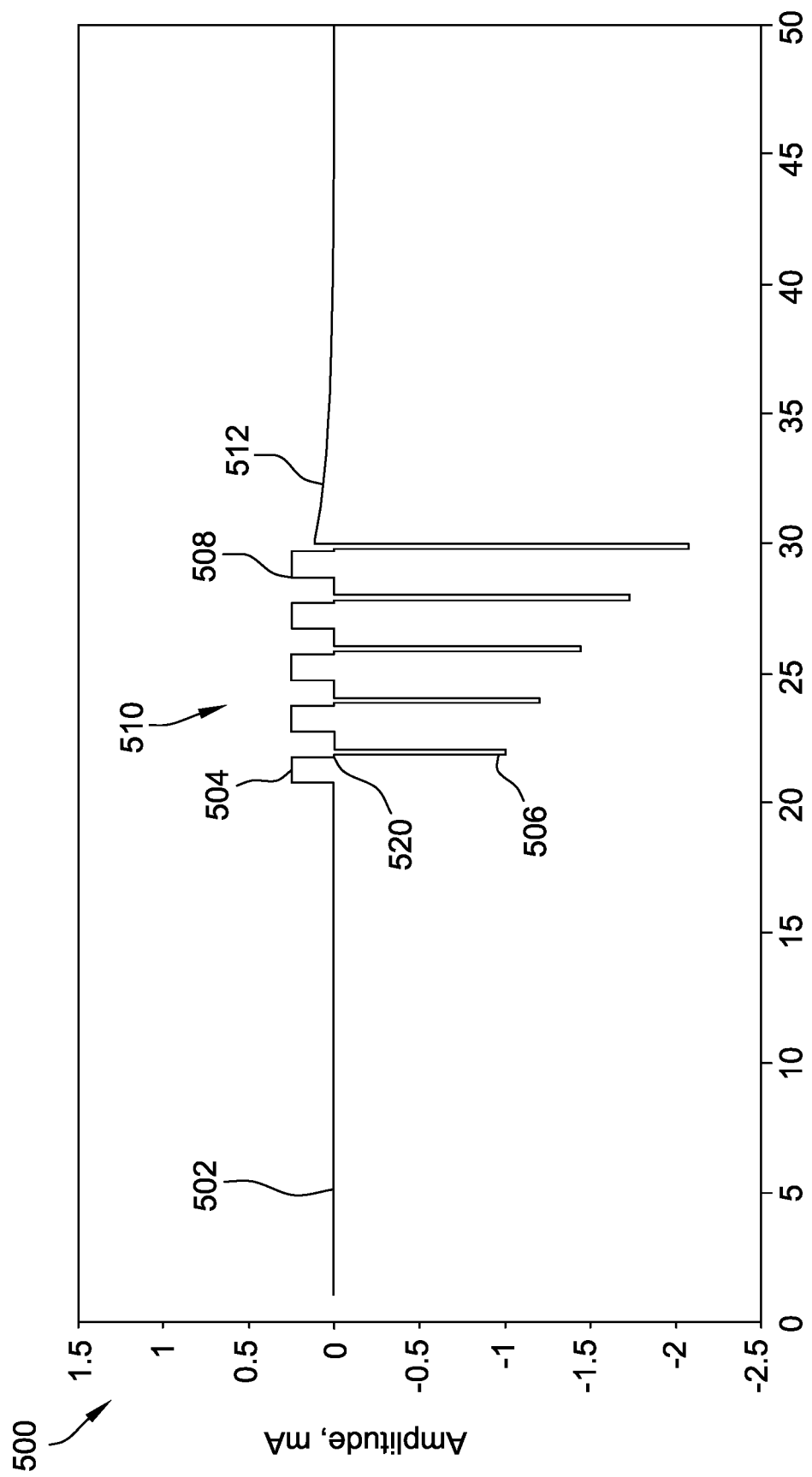
FIG. 5 is a graph illustrating one embodiment of an anodic-leading progressive burst waveform.

FIG. 5 is a graph 500 illustrating one embodiment of an anodic-leading progressive burst waveform 502. Waveform 502 includes a leading anodic pulse 504 with a fixed pulse width and amplitude.

Subsequent to leading anodic pulse 504, waveform 502 includes alternating cathodic pulses 506 and anodic pulses 508. In this embodiment, anodic pulses 508 each have the same pulse width and amplitude as leading anodic pulse 504. Further, cathodic pulses 506 each have the same pulse width, but the amplitude grows with each subsequent cathodic pulse 506.

Leading anodic pulse 504 and anodic pulses 508 may have a pulse width in a range from 400 µs to 1000 µs, for example, and an amplitude in a range from 12.5% to 50% of the amplitude of the first cathodic pulse 506. Further, cathodic pulses 506 may each have a pulse width in a range from 60 µs to 400 µs. For each burst 510, waveform 502 may include, for example, two to eight total anodic pulses (including leading anodic pulse 504 and anodic pulses 508), each anodic pulse followed by a corresponding cathodic pulse 506. Alternatively, any suitable parameters may be used.

In the embodiment shown in FIG. 5, the leading pulse of waveform 502 is anodic. However, those of skill in the art will appreciate that in a bipolar or multipolar simulation implementation, reference electrodes/return electrodes may exhibit waveform 502 in the opposite polarity (i.e., leading with a cathodic pulse).

Referring back to the embodiment of FIG. 5, to compensate for any additional charges accumulated due to the progressively growing cathodic pulses 506, a passive discharge 512 follows the last cathodic pulse 506 in burst 510. Further, in the embodiments described herein, the anodic pulse width is longer than the cathodic pulse width, and the charge output by leading anodic pulse 504 is less than or equal to the charge output by the first cathodic pulse 506. That is, the product of the amplitude and pulse width for leading anodic pulse 504 is less than or equal to the product of the amplitude and pulse width for the first cathodic pulse 506.

In some embodiments, waveform 502 includes an inter-phase gap 520 (e.g., in a range of 0 µs to 100 µs) between each anodic and cathodic pulse. Alternatively, inter-phase gap 520 is omitted.

Similar to waveform 302, depending on the particular application, the inter-burst frequency, the intra-burst frequency, and the pulse amplitudes of waveform 502 may be modified as appropriate.

In the example shown in FIG. 5, waveform 502 has an anodic pulse width of 1000 µs, a cathodic pulse width of 300 µs, an anodic pulse amplitude of 0.25 milliamps (mA), a first cathodic pulse amplitude of 1.0 mA, a cathodic pulse growth rate of 20% (i.e., the amplitude of each cathodic pulse is 20% larger than the amplitude of the immediately preceding cathodic pulse), an inter-phase gap of 100 µs, and an inter-burst frequency of 500 Hz. Alternatively, any suitable parameters may be used.

Waveform 502 provides an alternative technique of implementing charge buildup in bursting stimulation patterns, while utilizing an anodic-break stimulation scheme to improve stimulation of neuronal elements near the stimulation electrode. Waveform 502 may provide improved results in SCS, DRG stimulation, peripheral nerve stimulation, and DBS applications.

The embodiments described herein provide systems and methods for generating burst waveforms. An implantable neurostimulation system includes an implantable stimulation lead including a plurality of contacts, and an implantable pulse generator communicatively coupled to the stimulation lead. The pulse generator is configured to generate a waveform including a burst that includes a leading anodic pulse followed by alternating cathodic pulses and anodic pulses, each cathodic pulse in the burst having a greater amplitude than the previous cathodic pulse.

Although certain embodiments of this disclosure have been described above with a certain degree of particularity, those skilled in the art could make numerous alterations to the disclosed embodiments without departing from the spirit or scope of this disclosure. All directional references (e.g., upper, lower, upward, downward, left, right, leftward, rightward, top, bottom, above, below, vertical, horizontal, clockwise, and counterclockwise) are only used for identification purposes to aid the reader's understanding of the present disclosure, and do not create limitations, particularly as to the position, orientation, or use of the disclosure. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not limiting. Changes in detail or structure may be made without departing from the spirit of the disclosure as defined in the appended claims.

When introducing elements of the present disclosure or the preferred embodiment(s) thereof, the articles "a", "an", "the", and "said" are intended to mean that there are one or more of the elements. The terms "comprising", "including", and "having" are intended to be inclusive and mean that there may be additional elements other than the listed elements.

As various changes could be made in the above constructions without departing from the scope of the disclosure, it is intended that all matter contained in the above description or shown in the accompanying drawings shall be interpreted as illustrative and not in a limiting sense.

What is claimed is:

1. An implantable neurostimulation system for generating burst waveforms, the neurostimulation system comprising:
    an implantable stimulation lead comprising a plurality of contacts; and
    an implantable pulse generator communicatively coupled to the stimulation lead and configured to:
        generate a waveform including a burst that includes a leading anodic pulse followed by alternating cathodic pulses and anodic pulses, each cathodic pulse in the burst having a greater amplitude than the previous cathodic pulse, wherein the burst further includes a passive discharge following a last cathodic pulse, the passive discharge decaying from a positive value to zero.

2. The implantable neurostimulation system of claim 1, wherein the cathodic pulses are square wave cathodic pulses.

3. The implantable neurostimulation system of claim 1, wherein the leading anodic pulse and the subsequent anodic pulses have a same pulse width and amplitude, and wherein a total number of anodic pulses within the burst is in a range from two to eight pulses.

4. The implantable neurostimulation system of claim 1, wherein a pulse width of the leading anodic pulse is greater than a pulse width of the cathodic pulses, and wherein the pulse width of the leading anodic pulse is between 400 µs and 1000 µs.

5. The implantable neurostimulation system of claim 1, wherein the burst further includes an inter-phase gap between each anodic and cathodic pulse.

6. The implantable neurostimulation system of claim 1, wherein a charge output by the leading anodic pulse is less than or equal to a charge output by a first cathodic pulse.

7. The implantable neurostimulation system of claim 1, wherein an amplitude of the leading anodic pulse is in a range from 12.5% to 50% of an amplitude of a first cathodic pulse.

8. An implantable pulse generator for generating burst waveforms, the pulse generator comprising:
    a memory device; and
    a processor coupled to the memory device, the processor configured to generate a waveform including a burst that includes a leading anodic pulse followed by alternating cathodic pulses and anodic pulses, each cathodic pulse in the burst having a greater amplitude than the previous cathodic pulse, wherein the burst further includes a passive discharge following a last cathodic pulse, the passive discharge decaying from a positive value to zero.

9. The implantable pulse generator of claim 8, wherein the cathodic pulses are square wave cathodic pulses.

10. The implantable pulse generator of claim 8, wherein the leading anodic pulse and the subsequent anodic pulses have a same pulse width and amplitude, and wherein a total number of anodic pulses within the burst is in a range from two to eight pulses.

11. The implantable pulse generator of claim 8, wherein a pulse width of the leading anodic pulse is greater than a pulse width of the cathodic pulses, and wherein the pulse width of the leading anodic pulse is between 400 µs and 1000 µs.

12. The implantable pulse generator of claim 8, wherein the burst further includes an inter-phase gap between each anodic and cathodic pulse.

13. The implantable pulse generator of claim 8, wherein a charge output by the leading anodic pulse is less than or equal to a charge output by a first cathodic pulse.

14. The implantable pulse generator of claim 8, wherein an amplitude of the leading anodic pulse is in a range from 12.5% to 50% of an amplitude of a first cathodic pulse.

15. A method of applying neurostimulation, the method comprising:
    generating, using an implantable pulse generator, a waveform including a burst that includes a leading anodic pulse followed by alternating cathodic pulses and anodic pulses, each cathodic pulse in the burst having a greater amplitude than the previous cathodic pulse, wherein the burst further includes a passive discharge following a last cathodic pulse, the passive discharge decaying from a positive value to zero; and
    applying the waveform to a patient using an implantable stimulation lead coupled to the implantable pulse generator.

16. The method of claim 15, wherein the cathodic pulses are square wave cathodic pulses.

17. The method of claim 15, wherein the leading anodic pulse and the subsequent anodic pulses have a same pulse width and amplitude, and wherein a total number of anodic pulses within the burst is in a range from two to eight pulses.

18. The method of claim 15, wherein a pulse width of the leading anodic pulse is greater than a pulse width of the cathodic pulses, and wherein the pulse width of the leading anodic pulse is between 400 µs and 1000 µs.

19. The method of claim 15, wherein the burst further includes an inter-phase gap between each anodic and cathodic pulse.

20. The method of claim 15, wherein a charge output by the leading anodic pulse is less than or equal to a charge output by a first cathodic pulse.

* * * * *